US012728206B2

(12) United States Patent
Bruns

(10) Patent No.: US 12,728,206 B2
(45) Date of Patent: Sep. 8, 2026

(54) AUTO-INJECTOR

(71) Applicant: Owen Mumford Limited, Woodstock (GB)

(72) Inventor: Robert Williams Bruns, Woodstock (GB)

(73) Assignee: Owen Mumford Limited, Woodstock (GB)

( * ) Notice: Subject to any disclaimer, the term of this patent is extended or adjusted under 35 U.S.C. 154(b) by 1168 days.

(21) Appl. No.: 17/763,815

(22) PCT Filed: Sep. 22, 2020

(86) PCT No.: PCT/EP2020/076420
§ 371 (c)(1),
(2) Date: Mar. 25, 2022

(87) PCT Pub. No.: WO2021/058474
PCT Pub. Date: Apr. 1, 2021

(65) Prior Publication Data

US 2022/0401648 A1 Dec. 22, 2022

(30) Foreign Application Priority Data

Sep. 27, 2019 (GB) ..................................... 1914008

(51) Int. Cl.
*A61M 5/20* (2006.01)
*A61M 5/31* (2006.01)

(52) U.S. Cl.
CPC ............ *A61M 5/2033* (2013.01); *A61M 5/31* (2013.01); *A61M 2005/2013* (2013.01); *A61M 2005/202* (2013.01)

(58) Field of Classification Search
CPC .......... A61M 5/14566; A61M 5/14546; A61M 5/31515; A61M 2005/14506;
(Continued)

(56) References Cited

U.S. PATENT DOCUMENTS

| | | | |
|---|---|---|---|
| 4,681,566 | A | 7/1987 | Fenton, Jr. et al. |
| 2011/0172602 | A1 | 7/2011 | Eaton |
| 2013/0281936 | A1 | 10/2013 | Kemp et al. |

FOREIGN PATENT DOCUMENTS

| | | | |
|---|---|---|---|
| AU | 2013203107 | A1 | 5/2013 |
| CN | 102753225 | | 10/2012 |

(Continued)

OTHER PUBLICATIONS

International Search Report and Written Opinion of the International Searching Authority from corresponding PCT Application No. PCT/EP2020/076420 dated Feb. 11, 2021 (9 pages).

(Continued)

*Primary Examiner* — Theodore J Stigell
*Assistant Examiner* — Benjamin Koo
(74) *Attorney, Agent, or Firm* — Greenberg Traurig, LLP

(57) ABSTRACT

An auto-injector for receiving and operating a syringe, the auto-injector comprising a housing for receiving the syringe. The housing comprises a main body and a door operable into a first position and a second position, wherein the syringe is receivable within the housing when the door is in the first position. The door is configured to couple to: (i) a first plunger driver for priming thereof on a first movement of the door; and (ii) a second plunger driver for priming thereof on a second movement of the door. The first and second plunger drivers are configured on activation of the auto-injector to drive a plunger forward within the auto-injector to operate the syringe received within the auto-injector.

20 Claims, 7 Drawing Sheets

(58) Field of Classification Search
CPC .............. A61M 5/1454; A61M 5/1456; A61M 5/2033; A61M 2005/206; A61M 5/326; A61M 2005/2073; A61M 2005/2414; A61M 5/31; A61M 2005/2013; A61M 2005/202; A61M 5/31586; A61M 5/20
See application file for complete search history.

(56) References Cited

FOREIGN PATENT DOCUMENTS

| | | | |
|---|---|---|---|
| CN | 104768594 | A | 7/2015 |
| CN | 111278487 | | 6/2020 |
| EP | 2468341 | A1 | 6/2012 |
| EP | 2727617 | A1 | 5/2014 |
| GB | 2577682 | | 4/2020 |
| WO | 2010018411 | A1 | 2/2010 |
| WO | 2019032390 | | 2/2019 |
| WO | 2019099324 | | 5/2019 |

OTHER PUBLICATIONS

United Kingdom Intellectual Property Office, Combined Search and Examination Report Under Sections 17 and 18(3), for corresponding United Kingdom App. No. GB1914008.6, dated Feb. 28, 2020 [5 pgs].

India Intellectual Property, First Examination Report, for corresponding Indian Patent App. No. 202217023637, dated Feb. 28, 2025 [6 pgs].

China National Intellectual Property Administration, First Office Action, for corresponding Chinese Patent App. No. 202080067041.6, dated Apr. 28, 2023 [11 pgs].

AUTO-INJECTOR

CROSS-REFERENCE TO RELATED APPLICATIONS

The present application represents the United States National Stage of International Application No. PCT/EP2020/076420, filed Sep. 22, 2020, which claims priority to and the benefit of British Patent Application Serial No. GB 1914008.6, filed Sep. 27, 2019, and entitled, "AUTO-INJECTOR," the contents of which are incorporated herein by reference in their entirety.

TECHNICAL FIELD

The invention relates to auto-injectors for use with syringes. The invention may relate to, but need not be limited to, safety auto-injectors and/or auto-injectors for use with safety syringes.

BACKGROUND

Safety syringes typically include some form of safety mechanism to protect healthcare workers from a hypodermic needle of the syringe after it has been injected into a patient. Exemplary safety syringes may include a sheath for covering the needle after use of the syringe. Other exemplary syringes may cause the needle to retract within the barrel of the syringe.

Safety syringes may be broadly split into 'active' and 'passive' safety syringes. Active safety syringes typically require some action by a user of the syringe to engage the safety mechanism and/or deploy the sheath. Such action may be taken after removal of the needle from the patient, or may be taken during removal of the needle from the patient. Passive safety syringes typically engage the safety mechanism and/or deploy the sheath without any specific action by the user, that is, without any action other than that usually taken to use the syringe.

An auto-injector is a device for receiving a syringe and for driving a syringe plunger of the syringe into a barrel of the syringe without any force being applied by the user. Typically, an auto-injector includes a plunger driver and a drive spring that are arranged to provide a force to drive the syringe plunger into the barrel. The drive spring and plunger driver may be activated by operation of a button or other release mechanism on the auto-injector. A safety auto-injector may be one which includes a shroud that may be deployed to a position covering a needle of a syringe received within the auto-injector before and after use of the syringe. The shroud of the auto-injector may be deployed under a force applied by a shroud spring.

The force applied by a drive spring typically depends on the viscosity of the drug in the barrel. The more viscous a drug is, the greater the force the drive spring has to apply upon firing. The manual priming of an auto-injector with a high force drive spring can therefore be challenging if the force required to prime it is too high for a typical user of the auto-injector.

An improved auto-injector and method for priming thereof is required.

SUMMARY

According to an aspect of the invention there is provided an auto-injector for receiving and operating a syringe, the auto-injector comprising: a housing for receiving the syringe, the housing comprising a main body and a door operable into a first position and a second position, wherein the syringe is receivable within the housing when the door is in the first position; wherein the door is configured to couple to: (i) a first plunger driver for priming thereof on a first movement of the door; and (ii) a second plunger driver for priming thereof on a second movement of the door; the first and second plunger drivers being configured on activation of the auto-injector to drive a plunger forward within the auto-injector to operate the syringe received within the auto-injector.

The priming of the auto-injector is made easier by dividing the priming into first and second movements to reduce the force required to complete each movement.

Optionally, the first plunger driver comprises a first spring, and the second plunger driver comprises a second spring.

Optionally, the first spring comprises a compression spring, and/or the second spring comprises a tension spring.

Optionally, the syringe is receivable within the main body of the housing when the hinged door is in the first position.

Optionally, the main body and the door are connected by a hinge, and the auto-injector is provided with a charging link between the main body and the door, wherein the connection of the charging link to the main body and/or the connection of the charging link to the door is a slidable connection configured to slide when the door moves between the first and second positions, the charging link being configured to couple to the first and second plunger drivers for priming thereof on the respective first and second movements of the door.

Optionally, the main body and the door are connected by a sliding means, and the auto-injector is provided with a charging link between the main body and the door, wherein the connection of the charging link to the main body and/or the connection of the charging link to the door is a slidable connection configured to slide when the door moves between the first and second positions, the charging link being configured to couple to the first and second plunger drivers for priming thereof on the respective first and second movements of the door.

Optionally, the first position of the door is the open position, the second position of the door is the closed position, the first movement of the door is an opening movement, and the second movement of the door is a closing movement.

Optionally, the connection of the charging link to the door is fixed and the connection of the charging link to the main body is slidable.

Optionally, the connection of the charging link to the door is positioned at a point up to a half, up to a third, or up to a quarter of the length of the door from the hinge of the door.

Optionally, the main body and the connection of the charging link to the door are configured such that a maximum angle between the plane of the main body and the charging link during: (i) the first movement of the hinged door; and (ii) the second movement of the hinged door is up to 45 degrees.

Optionally, the force required for priming of the first plunger driver is less than the force required for priming of the second plunger driver.

Optionally, a combined driving force of the first and second plunger drivers is in the range from 30-50 Newtons.

Optionally, the charging link comprises a shuttle configured to travel along a shuttle guide to provide a slidable connection of the charging link to the main body.

Optionally, the shuttle comprises a first priming portion coupled to the first plunger driver and configured to travel along the shuttle guide in a first direction on the first movement of the door for priming the first plunger driver.

Optionally, the main body and/or the first priming portion comprises a latch configured to retain the first priming portion in position after the first movement of the door.

Optionally, the first plunger driver is primed under compression and is connected between the main body and the first priming portion.

Optionally, the shuttle comprises a second priming portion configured to travel along the shuttle guide in a second direction opposite the first direction on the second movement of the door for priming the second plunger driver.

Optionally, the charging link is configured to retain the second priming portion in position after the second movement of the door.

Optionally, the second plunger driver is primed under tension and is connected between the first priming portion and the second priming portion.

Optionally, the charging link is connected to the second priming portion.

Optionally, the first and second priming portions are configured to travel together along the shuttle guide on the first movement of the door, and are separable such that the second priming portion separates from the first priming portion and travels along the shuttle guide on the second movement of the door.

Optionally, the shuttle guide is coupled to the first and second plunger drivers such that movement of the first and second plunger drivers follows a path determined by the shuttle guide.

Optionally, the shuttle guide comprises a rod passing through the first plunger driver and passing through an aperture in the shuttle.

Optionally, the auto-injector comprises a ratchet operable during the second movement of hinged door to prevent movement of the door in the direction of the first position by a force exerted by the second plunger driver.

BRIEF DESCRIPTION OF THE DRAWINGS

Exemplary embodiments are disclosed herein with reference to the accompanying drawings, in which.

DETAILED DESCRIPTION

Generally, disclosed herein are exemplary methods and apparatus for auto-injectors. The term "auto-injector" is used herein and may be considered to encompass both an auto-injector and a safety auto-injector, as appropriate. The auto-injectors may be configured to receive and operate a standard syringe (i.e. not a safety syringe) and/or a safety syringe.

In the following embodiments, the terms "forward" and "front" refer to the patient facing end of the injection device or component thereof. In other words, the front end of the injection device is the end proximal to the injection site during use. Likewise, the term "rear" refers to the non-patient end of the injection device assembly or component thereof. In other words, the term "rear" means distant or remote from the injection site during use. Further, the term longitudinal is used to encompass a direction along or parallel to a longitudinal axis of the injection device.

Features of the exemplary arrangements disclosed herein are described as being "coupled" to other features. This term encompasses any coupling that results in the coupled features moving together in any direction, whether that be on a 1:1 basis or on some geared basis. The term "coupled" also encompasses any one of a connection between features, an abutment of one feature against another and an engagement of one feature with another, and such coupling may be direct or may be indirect, i.e. with a third feature therebetween.

In general terms, the invention is directed to assisting the priming of an auto-injector by using both the opening and closing movement of the auto-injector for priming thereof. An auto-injector may be considered primed when the plunger driver is in a configuration suitable to move the plunger of a syringe and thereby deliver medication using the auto-injector. A user may prime a plunger driver of an auto-injector by applying a force to the plunger driver. This may be done, for example by opening and closing a door of the auto-injector. Methods and apparatus disclosed herein use a force applied by a user when opening and closing the door to prime the plunger driver. In some arrangements, the plunger driver may comprise a plurality of biasing members (e.g. springs), one or more of the plurality being primed on opening of the door and one or more of the plurality being primed on closing of the door.

FIGS. 1*a*-1*f* show an exemplary auto-injector 100 for receiving and operating a syringe (not shown) during various stages of priming and firing.

Figure 1A:
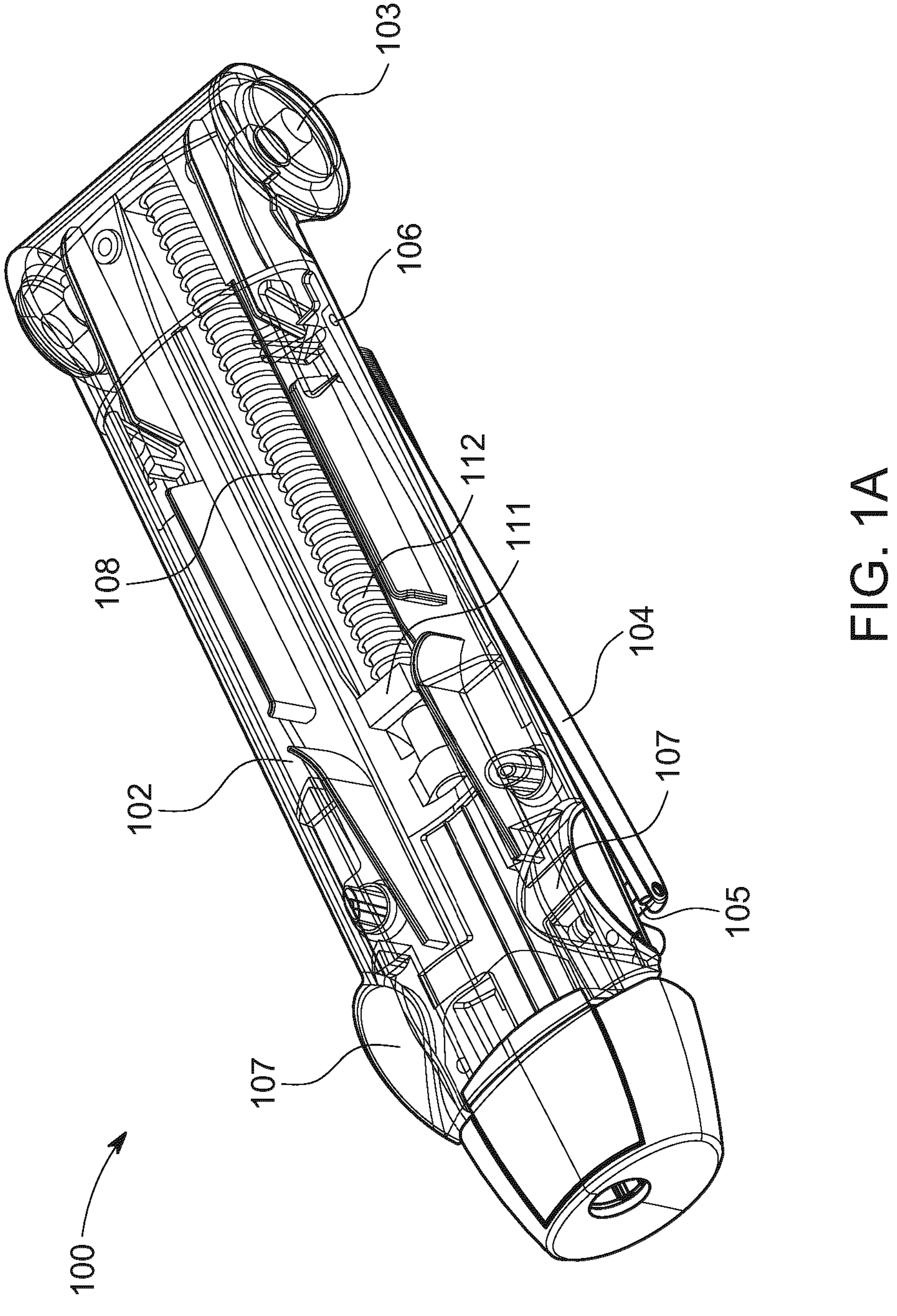
FIG. 1*a* shows a perspective view of an auto-injector.

The auto-injector 100 comprises a housing that further comprises a plurality of component parts. In the configuration of FIG. 1*a*, the housing comprises a main body 101 and a hinged door 102. The hinged door 102 is operable between an open position and a closed position. The hinged door 102 is in its closed position in FIG. 1*a*. A syringe (not shown) is receivable within the housing, for example, in the main body 101, when the hinged door 102 is in the open position.

The main body 101 and hinged door 102 are connected at a hinge 103. The door 102 is therefore rotatable relative to the main body 101. In FIGS. 1*a* to 1*f*, the hinge is located at the rear end of the main body 101 and the hinged door 102. In other arrangements, the hinge 103 may be positioned at locations further forward on one or both of the hinged door 102 and the main body 101.

At least one charging link 104 is connected between the main body 101 and the hinged door 102. FIGS. 1*a* to 1*f* show an exemplary auto-injector having two charging links 104. A connection 105 of the charging link 104 to the main body 101 is a slideable connection configured to slide on movement of the hinged door 102 between its open and closed positions. A connection 106 between the hinged door 102 and the charging link 104 is fixed with respect to its position on the hinged door 102. The connection 106 between the charging link 104 and the hinged door 102 is rotatable. The connection 106 is at a point on the hinged door 102 where when the hinged door 102 is open the connection 106 is rearward of the hinge 103 and when the hinged door 102 is closed the connection 106 is forward of the hinge 103 i.e. the connection 106 rotates about the hinge during opening and closing of the hinged door 106. In other arrangements, the connection 106 may be slidable and/or the connection 105 may be positionally fixed.

Optionally, the hinged door 102 comprises gripping features, which in the example shown comprise ergonometric handles 107. The gripping features may include any features that allow greater purchase for a user when pulling the hinged door 102 open and/or pushing the hinged door 102 closed. For example, the gripping features might include any type of handle, lip, flange or gripping surface for a user to open and/or close the hinged door 102.

The auto-injector 100 further comprises a first plunger driver 108. The first plunger driver 108 is configured to drive a plunger of a syringe received within the auto-injector 100 forwards to dispense a fluid from the syringe. In the example provided in FIGS. 1*a* to 1*f*, the first plunger driver 108 comprises at least one spring or other biasing member, which may be a tension spring, a compression spring or a torsion spring but in the example shown comprises a spring, which in this case is a compression spring.

The connection 105 is configured to couple to the first plunger driver 108 for priming thereof on an opening movement of the hinged door 102. That is, in the example shown in FIGS. 1*a* to 1*f*, upon opening the hinged door the slidable connection 105 slides rearward along the main body 101, thereby compressing the compression spring of the first plunger driver 108. The first plunger driver 108 may comprise a spring or a plurality of springs. As described below, the charging link 104 may comprise a shuttle 111 configured to travel along a shuttle guide 112 to provide the slideable connection of the charging link 104 to the main body 101.

The charging link 104, through its connections 105, 106 to the main body 101 and hinged door 102 converts the arc shaped movement of the hinged door 102 as it opens into a linear force (in this example in a rearward direction) on the first plunger driver 108 to prime it. The positioning of the connection 106 of the charging link 104 to the hinged door 102 and/or the length of the charging link 104 determine the level of mechanical advantage provided by this mechanism and can thereby make it easier for a user to prime the first plunger driver 108 during the opening movement of the hinged door. The longer the charging link 104 and the closer the connection 106 is positioned to the hinge 103, the shallower the maximum angle the charging link 104 forms with the main body 101 during the opening and/or closing movements of the hinged door 102. A shallower angle results in a greater mechanical advantage and allows the first plunger driver 108 to be primed more easily. This permits higher force springs to be used in the first plunger driver 108. It is noted, however, that there is a trade-off between having a shallow angle to increase mechanical advantage and having a steeper angle to increase the amount of rearward translation of the connection 105, but a decreased mechanical advantage.

Figure 1B:
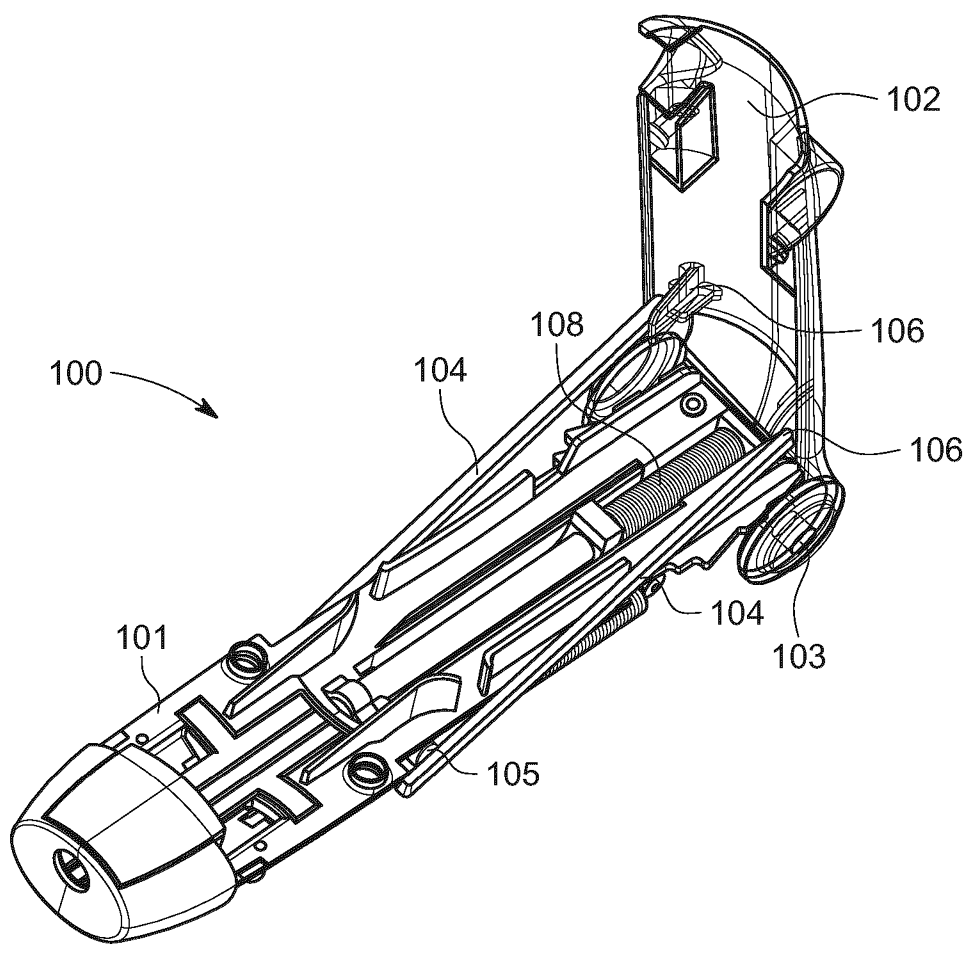
FIGS. 1*b*-1*c* show perspective views of an auto-injector undergoing priming.

FIG. 1*b* shows the hinged door 102 of the auto-injector 100 moving from a closed position to an open position. As the hinged door 102 moves in an arc, the connection 106 follows a path that ensures the angle between the charging link 104 and the main body provides a predetermined mechanical advantage during the opening movement.

Figure 1C:
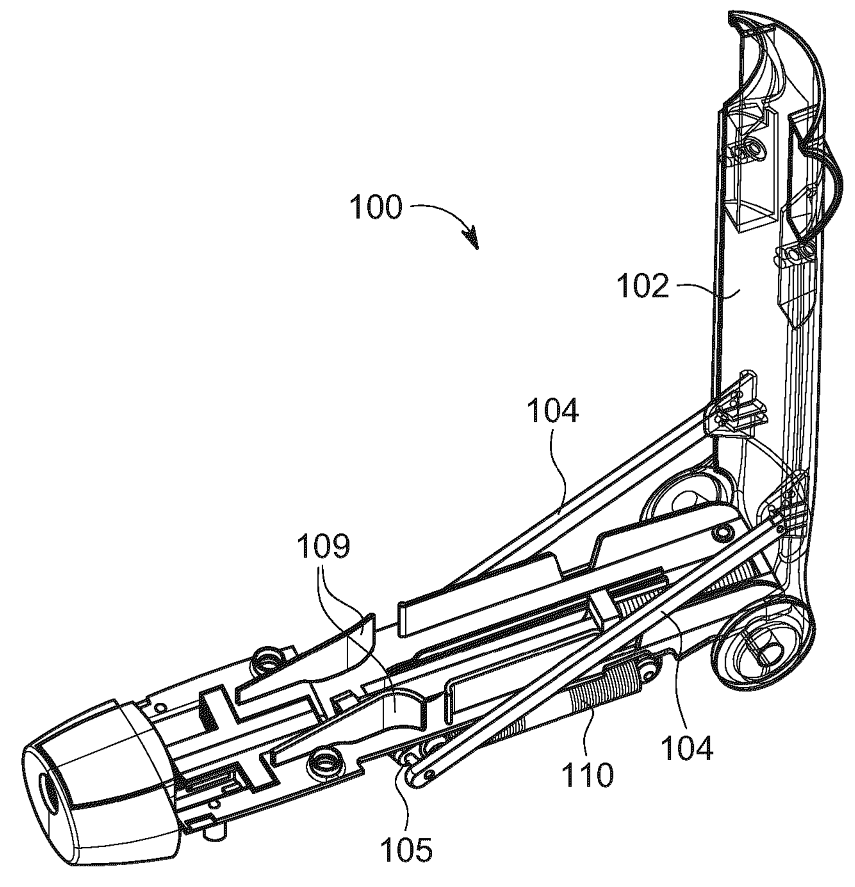

FIG. 1*c* shows the hinged door 102 of the auto-injector 100 in an open position. In the open position, a space in the main body 101 is provided into which a syringe (not shown) can be loaded. One or more internal support structures 109 may optionally be provided with which the syringe can be secured.

In the example provided in FIGS. 1*a* to 1*f*, the auto-injector 100 further comprises a second plunger driver 110, which may comprise a spring or a plurality of springs. In exemplary arrangements, the second plunger driver 110 comprises two springs. The two springs are tension springs.

The slidable connection 105 of the charging link 104 to the main body 101 is configured to couple to the second plunger driver 110 for priming thereof on a closing movement of the hinged door 102. The second plunger driver 110 may optionally be positioned in a different plane of the main body 101 to the first plunger driver 108. In the example provided, the second plunger driver 110 is positioned in a plane below the first plunger driver 108. By positioning the second plunger driver 110 in a different plane, the available space in the main body 101 for placing the syringe is increased. Further, the length of the charging link 104 is increased by extending it to the different plane.

As described above, during the opening movement of the hinged door 102, the charging link 104 is pulled in a rearwards direction by the hinged door 102 acting through the charging link's connection 106 to the hinged door 102. In turn, the charging link 104 through its slidable connection 105 to the main body slides along the main body in a rearwards direction to compress the compression spring of the first plunger driver 108. This primes the first plunger driver 108. Not only does the movement of the charging link in a rearwards direction prime the first plunger driver 108, but it also translates the second plunger driver 110 rearwardly without priming it. In the example provided in FIGS. 1*a* to 1*f*, the second plunger driver 110 slides with the charging link 104 in a rearwards direction without the tension springs being put under tension. The opening movement of the hinged door 102 thus only primes one of the two plunger drivers 108, 110.

Figure 1D:
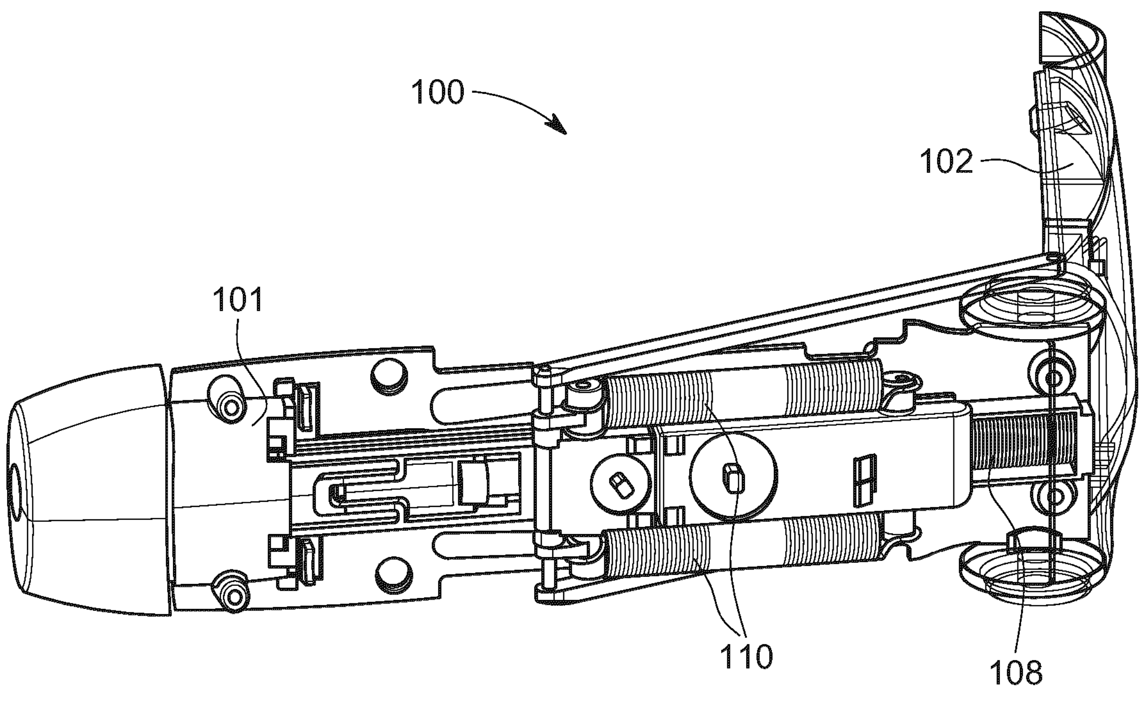
FIGS. 1*d*-1*e* show perspective views of an auto-injector undergoing priming.

FIG. 1*d* shows a perspective view of an underside of the auto-injector 100 when the hinged door 102 is in its open position. As can be seen in FIG. 1*d*, the compression spring of the first plunger driver 108 is in a primed, compressed state whereas the two tension springs of the second plunger driver 110 are in an un-primed, un-tensioned state.

Figure 1E:
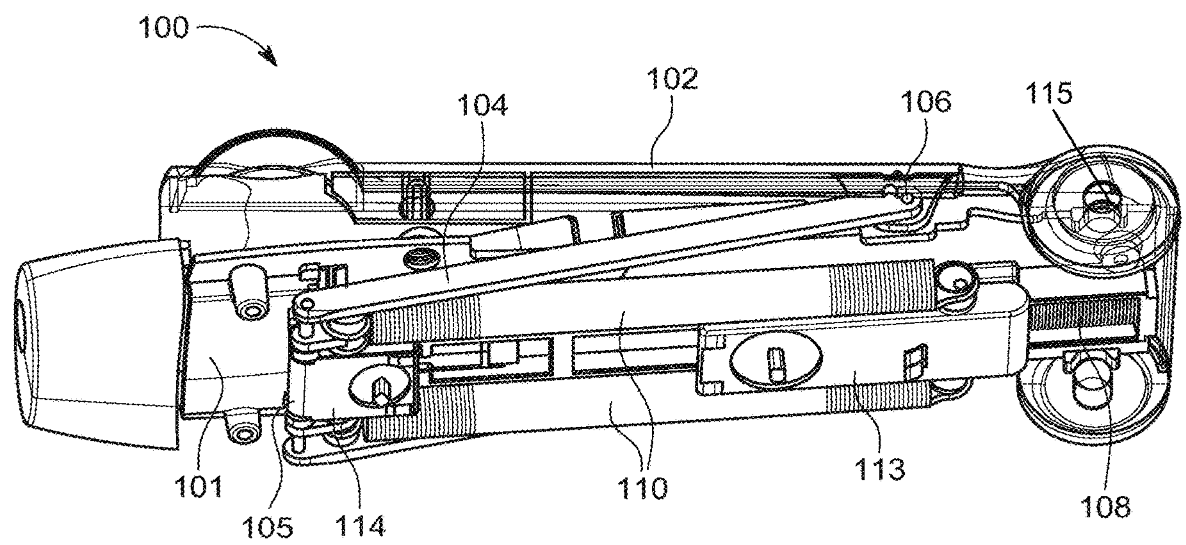

FIG. 1*e* shows the auto-injector 100 during the closing movement of the hinged door 102. As the hinged door 102 closes, the charging link 104 is pushed in a forward direction by the hinged door 102 acting through the connection 106. At the same time, the slideable connection 105 slides in a forward direction and pulls a first end of the tension spring of the second plunger driver 110 forward. A second end of the tension spring is retained in position and the second plunger driver 110 is therefore primed. The first plunger driver 108 is maintained in its primed state. In the example provided in FIG. 1*e*, the first plunger driver 108 is maintained in its primed state with a latch configured for this purpose.

As was the case when priming the first plunger driver 108, the charging link 104, through its connections 105, 106 to the main body 101 and hinged door 102 convert the arc shaped movement of the hinged door 102 as it closes into a linear force (in this example in a forward direction) on the second plunger driver 110 to prime it. The positioning of the connection 106 of the charging link 104 to the hinged door 102 and/or the length of the charging link 104 determine an amount of mechanical advantage provided by this mechanism and can thereby make it easier for a user to prime the device during the closing movement of the hinged door 102.

As is the case with the opening movement of the hinged door 102 described above, the positioning of the connection 106 of the charging link 104 to the hinged door 102 and/or the length of the charging link 104 determine the level of mechanical advantage provided by this mechanism and can thereby make it easier for a user to prime the second plunger driver 110 during the opening movement of the hinged door. The longer the charging link 104 and the closer the connection 106 is positioned to the hinge 103, the shallower the maximum angle the charging link 104 forms with the main body 101 during the opening and/or closing movements of the hinged door 102. A shallower angle results in a greater mechanical advantage and allows the second plunger driver 110 to be primed more easily. This permits higher force springs to be used in the second plunger driver 110, or a combined higher force of a plurality of springs.

Thus, in exemplary arrangements the connection 106 may be positioned, for example, at a point up to a half, up to a third, up to a quarter, or up to a smaller fraction of the length of the hinged door 102 from a hinge of the hinged door 102. The smaller the fraction, the greater the mechanical advantage. For example, a connection at a point up to a quarter of the length of the hinged door 102 will provide a greater mechanical advantage over a connection that is half way along the hinged door 102 from hinge 103.

The main body 101 and the connection 106 of the charging link 104 to the hinged door 102 are configured such that a maximum angle between the plane of the main body 101 and the charging link 104 during the opening movement and/or closing movement of the hinged door 102 is up to 45 degrees. Typically, the maximum angle of the charging link 104 will be achieved when the hinged door 102 is perpendicular to the main body 101. Other maximum angles are possible, for example, the maximum angle may be up to 35 degrees, 25 degrees or 15 degrees.

Figure 1F:
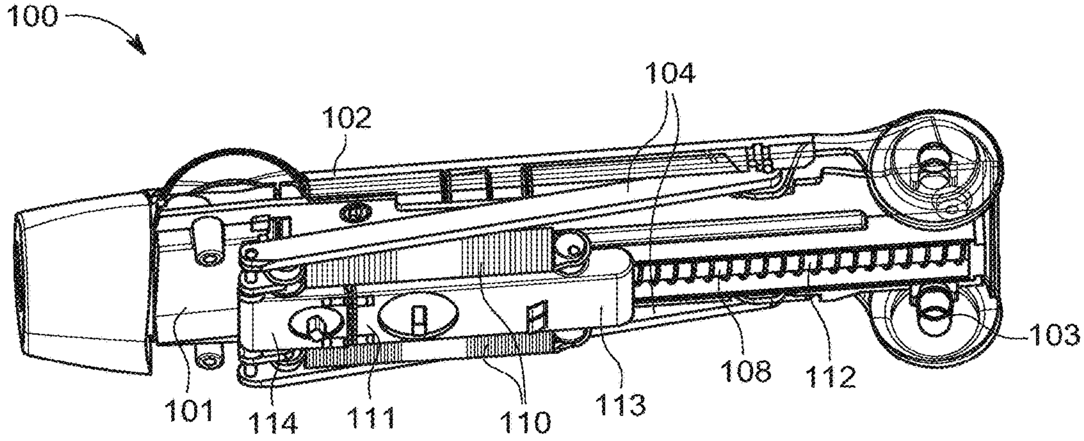
FIG. 1*f* shows a perspective view of an auto-injector after firing.

FIG. 1*f* shows the auto-injector 100 after activation. The first plunger driver 108 and second plunger driver 110 are configured upon activation of the auto-injector 100 to drive a plunger forward within the auto-injector 100 to operate a syringe received within the auto-injector 100. In the example of FIGS. 1*a* to 1*f*, the compression spring of the first plunger driver 108 and the two tension springs of the second plunger driver 110 work together to provide the forward force necessary to cause a drug in the mounted syringe to be injected into a patient.

The plunger of the syringe may be coupled to the first and second plunger drivers 108, 110 to achieve this. Auto-injectors described herein divide the priming movement into two separate, lower force movements: the opening and the closing of the hinged door. In this way an injection force applied by the plunger drivers to the plunger can be high, for example in the range of 30-50 Newtons. The maximum force a user needs to apply at any point to prime the plunger drivers may be lower, for example in a range of 3-25 Newtons. Preferably the maximum force a user needs to apply at any point to prime the plunger driver is between 3 and 7 Newtons, and even more preferably the force a user needs to apply at any point to prime the plunger drivers is 5 Newtons. In contrast, in known devices the maximum drive spring strength is typically limited to the force a user can reasonably apply during a single priming movement.

The contribution the first plunger driver 108 makes to the injection force need not be (but can be) equal to the contribution made by the second plunger driver 110. In one configuration, as it is typically easier for a user to apply a higher force on a closing movement the hinged door 102 as they can use their palm to push the door closed, the second plunger driver 110 may provide a greater driving force than the first plunger driver 108. In this case, the force required for priming of the first plunger driver 108 is less than the force required for priming of the second plunger driver 110.

Further optional features and components will now be described with reference to FIG. 1*f*.

The charging link 104 may be coupled to a shuttle 111. The shuttle 111 may be slidable along the main body 101 and configured to travel along a shuttle guide 112. The connection 106 may be between the charging link 104 and the shuttle 111 and may be rotatable. In some arrangements, the shuttle 111 provides the slideable connection of the charging link 104 to the main body 101.

The shuttle 111 comprises a first priming portion 113 and a second priming portion 114. The first plunger driver (e.g. compression spring) 108 is connected at a first end to the main body and at a second end to the first priming portion 113. The second plunger driver (e.g. tension springs) is connected at a first end to the first priming portion 113 and at a second end to the second priming portion 114. The first and second priming portions 113, 114 are configured to travel along the shuttle guide 112 together towards the hinge 103 upon opening of the hinged door 102. As the compression spring of the first plunger driver 108 is connected between the main body 101 and the first priming portion 113, this motion primes the first plunger driver 108. As the tension springs of the second plunger driver 110 are connected between the first and second priming portions, this movement does not prime the second plunger driver 110.

The main body 101 and/or the first priming portion 113 may comprise a latch configured to retain the first priming portion 113 in position on the shuttle guide 112 after opening of the hinged door 102. The first and second priming portions 113, 114 are separable after opening of the hinged door 102. This separated state is shown in FIG. 1*e*. The second priming portion 114 is configured to travel along the shuttle guide 112 away from the hinge 103 upon closing of the hinged door 102. Because the tensions springs are connected between the first and second priming portions 113, 114, as the second priming portion 114 travels forward the tension springs of the second plunger driver 110 are primed.

Upon firing, caused for example by pressing the front end of the auto-injector 100 on a patient's skin or via some other firing mechanism, the separated first priming portion 113 is released from its latch and travels forward along the shuttle guide 112 under the combined force of the first plunger driver 108 and second plunger driver 110. In the example of FIG. 1*f*, the compression spring pushes and the tension springs pull the first priming portion 113 of the shuttle 111 in a forward direction. As shown in FIG. 1*f*, the shuttle guide 112 is coupled to the first and second plunger drivers 108, 110 such that movement thereof follows a path determined by the shuttle guide 112. In the example of FIG. 1*f*, the shuttle guide comprises a rod passing through the first plunger driver 108 and passing through an aperture in the shuttle 111.

The auto-injector 100 may also comprise a shroud at least partially covering and extending forwards beyond a forward end of a needle of the syringe when the syringe is fitted within the auto-injector and before use. When present, the shroud may be configured, upon rearward movement thereof, for example caused by pressing of the shroud onto a patient's skin, to release the latch and fire the device. Other firing mechanisms envisaged include side or rear buttons.

The auto-injector 100 may also comprise a ratchet 115 operable during the closing movement of the hinged door 102 to prevent movement of the hinged door in the opening direction by a force exerted by the second plunger driver 110. With reference to FIG. 1 *e*, as the door is moved to its closed position and the second plunger driver 110 becomes primed, the second plunger driver 110 exerts an opposing force against the closing hinged door 102. If a user does not maintain a force on the hinged door 102 during closing before it is fully closed, it will spring back open. The ratchet 115 prevents this from happening by permitting movement of the hinged door 102 in a closing direction but preventing it in the opening direction. The ratchet 115 is configured to become operable only after the user has opened the door for the first time so that it does not interfere with a user's ability to open the hinged door 102 in order to load the syringe into the main body 102.

The skilled person will be able to envisage other assemblies, auto-injectors and features thereof without departing from the scope of the appended claims. In particular, it is noted that one or more features included in one or more drawings may be integrated into auto-injectors shown in other drawings, as will be appreciated by the skilled person.

Figure 2A:
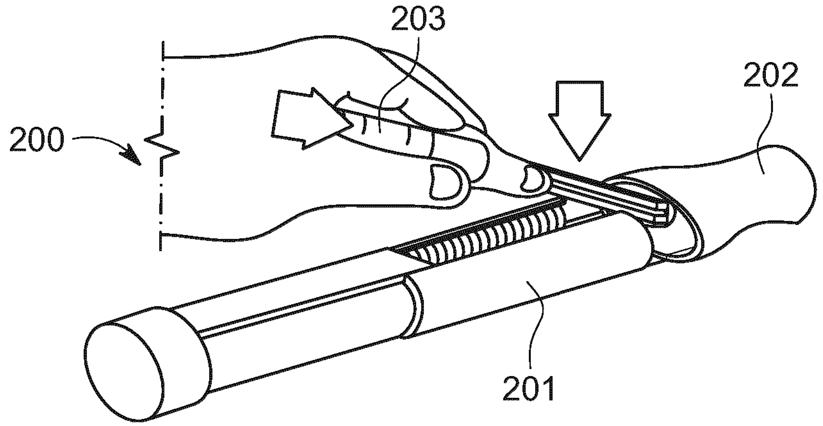
FIGS. 2*a*-2*d* show perspective views of an auto-injector undergoing priming and firing.
Figure 2B:
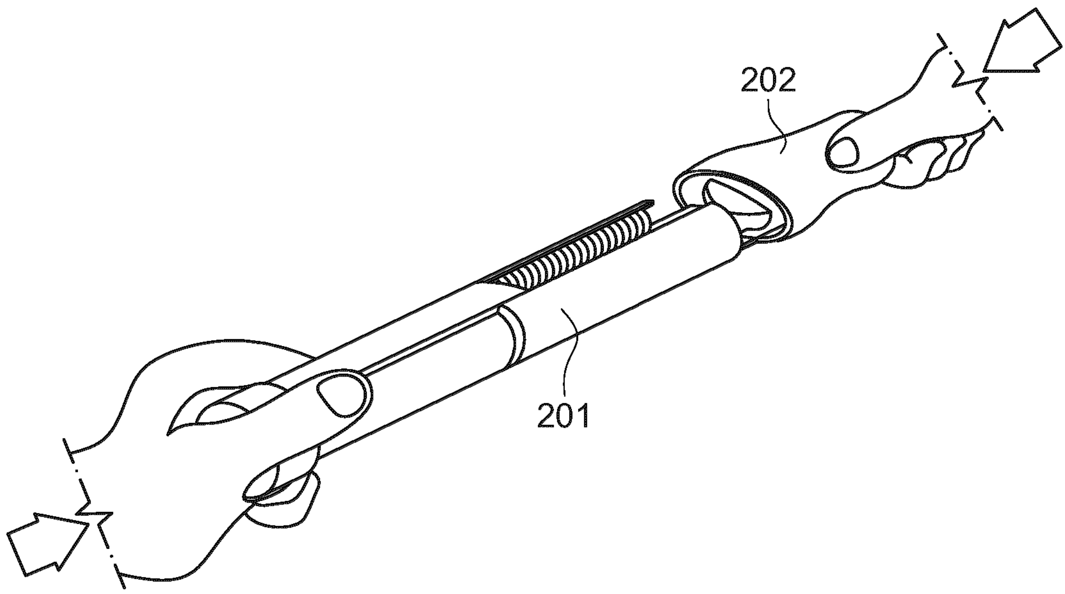
Figure 2C:
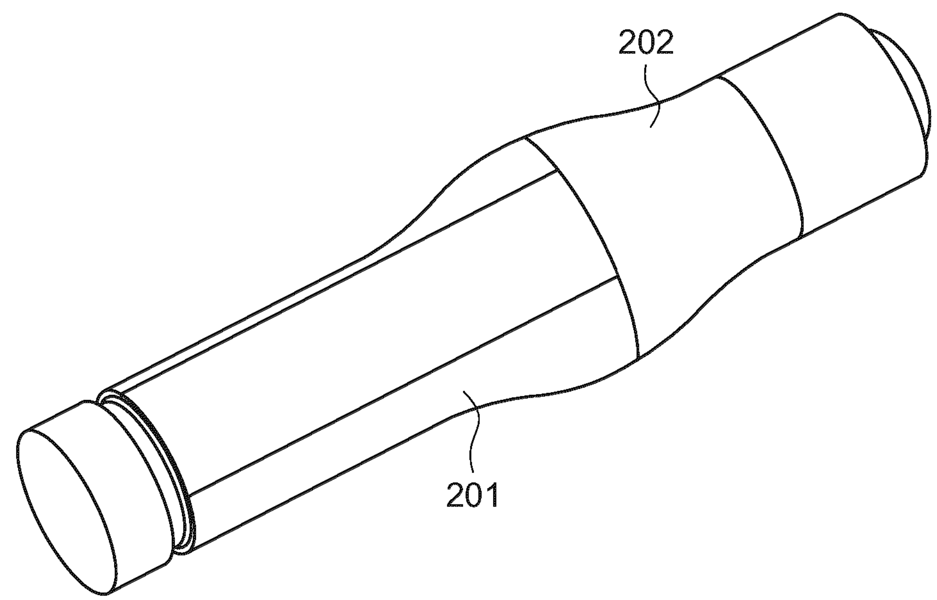
Figure 2D:
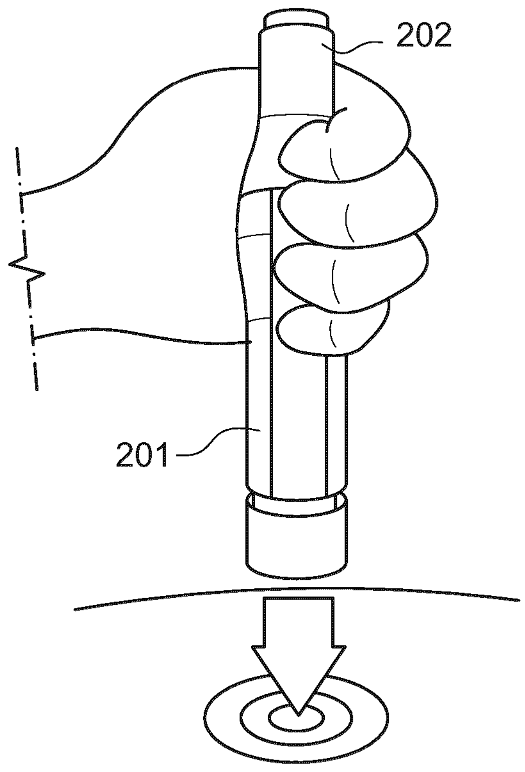

Although the present invention has been described with reference to a hinged door it may be understood that other door configurations are possible. For example the main body and door may have a slideable connection as illustrated in the example auto-injector 200 of FIGS. 2*a* to 2*d*. Such an auto-injector 200 will function in the same way as described previously with reference to FIGS. 1 to 4. The main body 201 and door 202 may be connected by any suitable means, for example a projection from the door 202 may be received within the main body 201. As was the case in the example configurations of FIGS. 1*a* to 1*f*, a charging link between the main body and door may be provided. The charging link may be configured to slide when the door 202 is moved between the first and second positions as shown in the transition between FIGS. 2*b* and 2*c*. The charging link may be configured to couple to the first and second plunger drivers of the auto-injector 200 for priming thereof on a respective first and second movement of the door to achieve the advantages described herein.

In the example configurations of FIGS. 2*a*-2*d*, the first position of the auto-injector is the open position and a syringe 203 may be loaded into the auto-injector 200 when it is in its open position. After the syringe 203 is loaded, the door may be moved towards its second position, in this case the closed position. The auto-injector may then be fired by pressing a front end onto the surface of a user's skin, or by a different firing mechanism such as a button.

The invention claimed is:

1. An auto-injector for receiving and operating a syringe, the auto-injector comprising:

a housing for receiving the syringe, the housing comprising a main body and a door operable into a first position and a second position, wherein the syringe is receivable within the housing when the door is in the first position;

wherein the door is configured to couple to:

(i) a first plunger driver for priming thereof on a first movement of the door, the first plunger driver comprising a first spring; and (ii) a second plunger driver for priming thereof on a second movement of the door, the second plunger driver comprising a second spring;

the first and second plunger drivers being configured on activation of the auto-injector to drive a plunger forward within the auto-injector to operate the syringe received within the auto-injector, and a ratchet operable during the second movement of the door to prevent movement of the door in the direction of the first position by a force exerted by a second plunger driver, wherein the first position of the door is an open position, wherein the second position of the door is a closed position, wherein the first movement of the door is an opening movement, and wherein the second movement of the door is a closing movement.

2. An auto-injector according to claim 1, wherein the first spring comprises a compression spring, and/or the second spring comprises a tension spring.

3. An auto-injector according to claim 1, wherein the syringe is receivable within the main body of the housing when the door is in the first position.

4. An auto-injector according to claim 1, wherein the force required for priming of the first plunger driver is less than the force required for priming of the second plunger driver.

5. An auto-injector according to claim 1, wherein a combined driving force of the first and second plunger drivers is in the range from 30-50 Newtons.

6. An auto-injector according to claim 1, wherein the main body and the door are connected by a hinge, and the auto-injector is provided with a charging link between the main body and the door, wherein the connection of the charging link to the main body and/or the connection of the charging link to the door is a slidable connection configured to slide when the door moves between the first and second positions, the charging link being configured to couple to the first and second plunger drivers for priming thereof on the respective first and second movements of the door.

7. An auto-injector according to claim 6, wherein the connection of the charging link to the door is fixed and the connection of the charging link to the main body is slidable.

8. An auto-injector according to claim 6, wherein the connection of the charging link to the door is positioned at a point up to a half, up to a third, or up to a quarter of the length of the door from the hinge of the door.

9. An auto-injector according to claim 6, wherein the main body and the connection of the charging link to the door are configured such that a maximum angle between the plane of the main body and the charging link during:

(i) the first movement of the hinged door; and (ii) the second movement of the hinged door is up to 45 degrees.

10. An auto-injector according to claim 6, wherein the charging link comprises a shuttle configured to travel along a shuttle guide to provide a slidable connection of the charging link to the main body.

11. An auto-injector according to claim 10, wherein the shuttle guide is coupled to the first and second plunger drivers such that movement of the first and second plunger drivers follows a path determined by the shuttle guide.

12. An auto-injector according to claim 10, wherein the shuttle comprises a first priming portion coupled to the first plunger driver and configured to travel along the shuttle guide in a first direction on the first movement of the door for priming the first plunger driver.

13. An auto-injector according to claim 12, wherein the main body and/or the first priming portion comprises a latch configured to retain the first priming portion in position after the first movement of the door.

14. An auto-injector according to claim 12, wherein the first plunger driver is primed under compression and is connected between the main body and the first priming portion.

15. An auto-injector according to claim 12, wherein the shuttle comprises a second priming portion configured to travel along the shuttle guide in a second direction opposite the first direction on the second movement of the door for priming the second plunger driver.

16. An auto-injector according to claim 15, wherein the charging link is configured to retain the second priming portion in position after the second movement of the door.

17. An auto-injector according to claim 15, wherein the charging link is connected to the second priming portion.

18. An auto-injector according to claim 15, wherein the second plunger driver is primed under tension and is connected at a first end to the first priming portion and at a second end to the second priming portion.

19. An auto-injector according to claim 18, wherein the first and second priming portions are configured to travel together along the shuttle guide on the first movement of the door, and are separable such that the second priming portion separates from the first priming portion and travels along the shuttle guide on the second movement of the door.

20. An auto-injector according to claim 19, wherein the shuttle guide comprises a rod passing through the first plunger driver and passing through an aperture in the shuttle.

* * * * *